United States Patent [19]

Schmehl

[11] Patent Number: 5,354,370
[45] Date of Patent: Oct. 11, 1994

[54] TISSUE PROCESSOR

[75] Inventor: Stewart Schmehl, Montclair, N.J.

[73] Assignee: Hacker Industries, Inc., Fairfield, N.J.

[21] Appl. No.: 870,052

[22] Filed: Apr. 15, 1992

[51] Int. Cl.$^5$ .............................................. B05C 3/02
[52] U.S. Cl. .................................. 118/50; 118/421; 118/429; 118/696
[58] Field of Search ............... 118/429, 50, 421, 704, 118/692, 693, 694, 712, 696; 422/110, 292

[56] References Cited

U.S. PATENT DOCUMENTS

| | | | |
|---|---|---|---|
| Re. 29,073 | 12/1976 | Kinney et al. | 118/698 |
| 2,392,229 | 1/1946 | Cohen | 118/693 |
| 2,853,084 | 9/1958 | Lipshaw | 134/76 |
| 3,227,130 | 1/1966 | Weiskopf | 118/697 |
| 3,446,423 | 5/1969 | Carroll | 137/565 |
| 3,557,077 | 1/1971 | Brunfeldt et al. | 530/334 |
| 3,604,436 | 8/1971 | Lipshaw | 134/76 |
| 3,725,010 | 4/1973 | Penhast | 422/64 |
| 3,762,362 | 10/1973 | Lipshaw | 118/666 |
| 3,892,197 | 7/1975 | Kinney et al. | 118/50 X |
| 4,001,460 | 1/1977 | Kinney et al. | 427/2 |
| 4,003,708 | 1/1977 | Taguchi et al. | 422/81 |
| 4,141,312 | 2/1982 | Louder et al. | 118/702 |
| 4,483,270 | 11/1984 | Toya et al. | 118/429 X |
| 4,604,964 | 8/1986 | Gordon et al. | 118/50 |
| 4,788,043 | 11/1988 | Kagiyama et al. | 422/292 |
| 4,801,553 | 1/1989 | Owen et al. | 436/174 |
| 5,035,200 | 7/1991 | Moriyama et al. | 118/693 |
| 5,049,510 | 9/1991 | Repasi et al. | 118/429 X |

OTHER PUBLICATIONS

Fisher Scientific Product Bulletin, 6-370, (1964).
Lipshaw Catalogue No. 73, Lipshaw Manufact. Corp., Detroit, Mich., pp. F1-F6, (1973).

*Primary Examiner*—David A. Simmons
*Assistant Examiner*—J. Sells

[57] ABSTRACT

A tissue processor having a process chamber and at least one liquid reservoir. At least one auxiliary reservoir is connected between the process chamber and the at least one liquid reservoir. There is a means to drive liquid from the at least one liquid reservoir to the auxiliary reservoir, and from the auxiliary reservoir to the process chamber. Preferably, there is a second auxiliary reservoir and means to drive fluid from the process chamber back to the liquid reservoir. The apparatus and related method are useful to treat and fix biological tissue samples for microscopic examination.

17 Claims, 4 Drawing Sheets

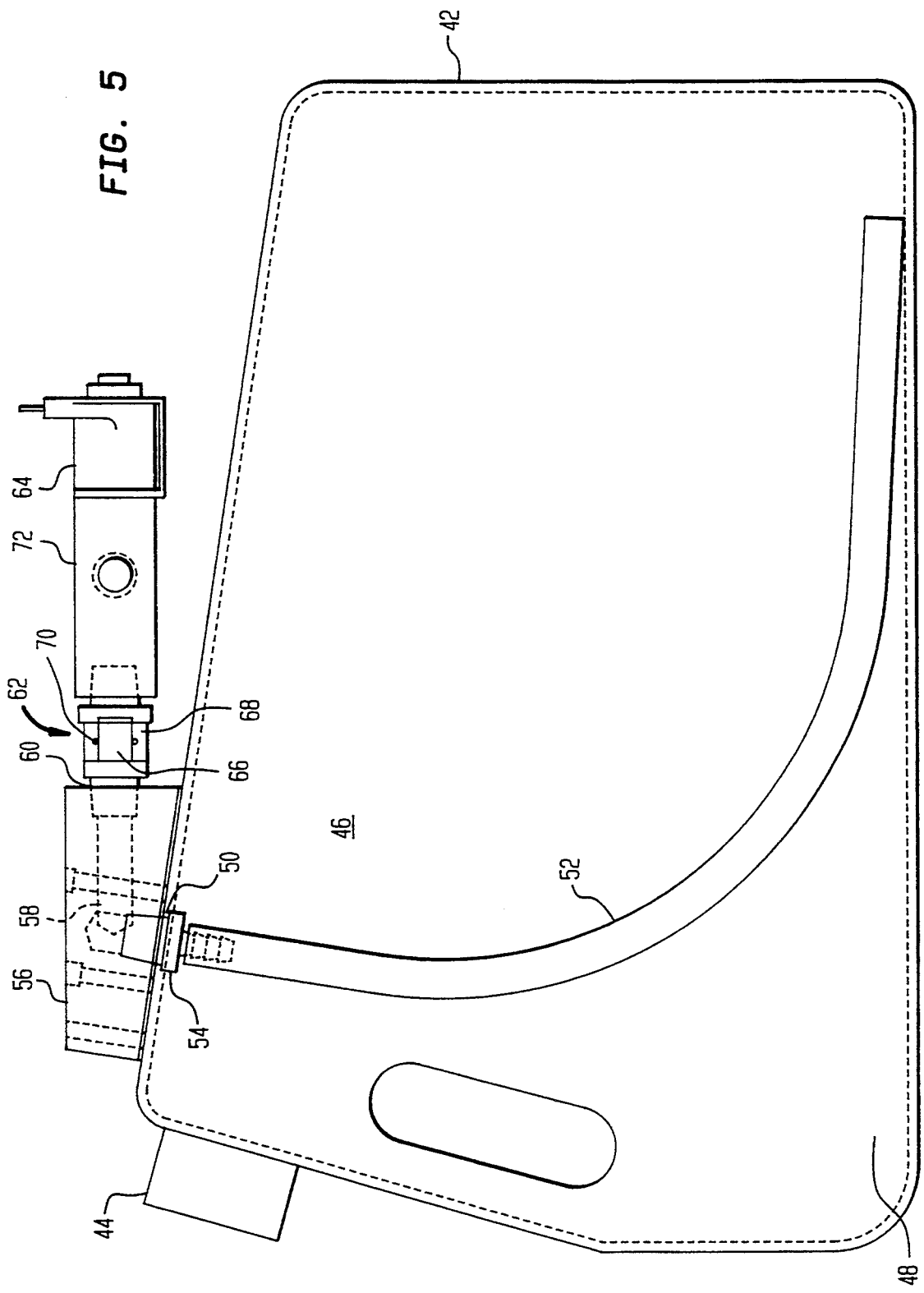

TISSUE PROCESSOR

BACKGROUND OF THE INVENTION

1. Field of the Invention

The present invention relates to an improved tissue processor apparatus and related method; more particularly the present invention relates to an improved which minimizes the deterioration of the tissue during the transition between processing steps.

2. Description of the Related Art

Tissue processors are used to condition samples of tissue for microscopic examination. The tissue samples are typically fragile biological samples which can easily be damaged. The samples are prepared by being sequentially exposed to fixing, treating or staining liquids. As part of the preparation, the samples are embedded in a vehicle that gives the specimen structural integrity. A useful vehicle is a paraffin wax which is applied in a molten form.

The tissue samples are placed in a process chamber. The chamber is sealed and filled and drained with various processing reagents. The samples are finally submerged in molten paraffin wax. The samples are thereby subjected to continually changing thermal conditions the feeding and removal from the process chamber of a variety of liquids which can include molten paraffin wax. The fragile tissue samples can be damaged during the immersion and removal of liquids including molten paraffin wax. Because the tissue samples are typically biological in nature they are susceptible to thermal degradation. That is, if the tissue samples are subjected to unwanted high temperatures they can "cook". This can occur when the chamber is empty and being preheated to receive the next liquid in sequence which can include molten paraffin wax. A continuing goal is to prepare tissue samples using a process which minimizes or prevents sample deterioration.

U.S. Re. Ser. No. 29,073 and U.S. Pat. No. 4,000,460 describe a tissue processing apparatus and method. These references disclose the use of a plurality of containers of treating liquids, including paraffin. The tissue specimens are confined in the processing chamber under sealed cover and remain stationary during processing. The various liquids are directed to the processing chamber in a programmed seqence. Liquids are drawn to a sealed processing chamber by vacuum in the chamber and returned to the containers by pressure applied to the chamber. Containers of liquid paraffin wax are arranged in immediate proximity to the processing chamber. This keeps the processing chamber at a higher temperature so that the paraffin is received and remains in molten form in the chamber.

According to the disclosed method vacuum is applied to the process chamber to draw reagent liquid into the chamber from a reagent container. When the reagent container is empty, air is drawn into the process chamber, increasing the chamber pressure. The increase in chamber pressure is detected and indicates to the system that all of the liquid has been transferred. However, the air drawn through the bottom of the process chamber agitates and can damage the tissue.

Another problem with existing tissue processors is the time to transfer reagents and paraffin from their respective containers to the process chamber and back. It can take on the order of five minutes to fill and drain the process chamber. As a result, those tissue samples located in the upper portion of the process chamber can be left exposed, i.e. not in contact with liquid for up to ten minutes per processing step of which there can be up to fifteen. This can result in significant discrepancies in the quality of the processed tissue samples within the same batch depending upon their location in the process chamber.

In the disclosed processes molten paraffin is drawn to the process chamber. However the chamber must be preheated and void of other liquid. If these conditions are not met, paraffin entering the bottom of the process chamber will solidify and prevent further filling of the chamber. Further, the preheating of the process chamber in the absence of liquids causes samples to be exposed to excessive heat which can cook the tissue.

There is disclosed a method for controlling liquid level in the process chamber by applying a vacuum for a predetermined time period. This method is inaccurate due to differences in liquid paths in the system. This can result in exposed tissue when not enough liquid is brought to the process chamber.

The disclosed processes have the disadvantages of sample deterioration by both liquid movement and by heat transfer. These are attributable to the sequential addition and removal of liquids which physically contact the samples. Additionally, the introduction of molten paraffin into the process chamber typically requires preheating the chamber to prevent paraffin solidification. This preheating can "cook" the sample.

SUMMARY OF THE INVENTION

The present invention relates to an tissue processor apparatus and method of operation. The improved tissue processor has features which minimize deleterious physical and thermal effects of processing on tissue samples.

The tissue processor apparatus of the present invention comprises a support frame or cabinet. There is at least one, and preferably one, temperature controlled process chamber supported on the frame. At least one, and preferably a plurality of liquid reservoirs are connected to communicate with the process chamber. At least one, and preferably two auxiliary reservoirs are connected between the process chamber and the at least one liquid reservoir. Most preferably, at least one first auxiliary reservoir is connected between the process chamber and the at least one liquid reservoir, and at least one second reservoir is separately connected between the process chamber and the at least one liquid reservoir. There are means to drive liquid from at least one liquid reservoir to the first auxiliary reservoir and from the first auxiliary reservoir to the process chamber. Preferably, there are means to drive liquid back from the process chamber to the second auxiliary reservoir, and from the second auxiliary reservoir to at least one liquid reservoir.

The apparatus can further comprise at least one heated reservoir connected to the process chamber. As with the liquid reservoirs the heated reservoirs are preferably connected to the process chamber through at least one auxiliary reservoir and more preferably through the first and second auxiliary reservoirs.

Specific and preferred embodiments of the present invention comprise features to minimize exposure to a heated atmosphere in the process chamber in the absence of liquid and to minimize time between the feeding and removal of liquid. The heated reservoir and auxiliary reservoirs are located so that there is substantially no heat transfer between the process chamber and the heated reservoirs. This prevents the heated reservoirs from introducing unwanted heat into the process chamber. Additionally, there cam be a means to measure and control the liquid level in the process chamber.

In a particularly preferred embodiment a manifold is connected to communicate with the process chamber and at least two liquid reservoirs are connected to communicate with the process chamber through the manifold. This makes construction more efficient and helps to transfer liquids more effectively.

The means to drive liquid from the liquid reservoir, as well as heated liquid, such as molten paraffin wax from the heated reservoirs to the process chamber through the auxiliary reservoir can be a pressure and/or vacuum pump. This same means can be used to drive the liquid from the process chamber. The liquid or molten wax is driven from the process chamber back to a respective heated or liquid reservoir. It is particularly preferred to feed the liquid to the process chamber under pressure by a suitable pressure pump, and remove or drive the liquid from the process chamber under a vacuum by a suitable vacuum means such as a vacuum pump. Preferably, the liquid is fed into the top of the process chamber and removed from the bottom of the process chamber. The use of a pressure liquid feed from the top results in the liquid rising through the tissue specimens with a minimum of sample disruption. While the removal of liquid under a vacuum likewise helps to minimize sample disruption. Preferably, the pressure chamber has a vent to the atmosphere so that the pressure in the process chamber can be maintained at atmospheric pressure.

The liquids used to treat the tissue samples include liquid reagents typically used. These include fixing, processing, staining and cleaning liquids. The heated liquid can be paraffin wax use to saturate and give structure to the tissue sample.

The present invention additionally includes a method comprising placing at least one tissue sample into a temperature controlled process chamber of a tissue processor. Tissue treatment liquid is fed from at least one liquid reservoir connected to at least one auxiliary liquid reservoir. The tissue treatment liquid is fed from the auxiliary liquid reservoir to the process chamber. The method can further comprise feeding a heated liquid, such as paraffin, to at least one auxiliary reservoir connected to communicate with the process chamber and feeding the molten paraffin to the auxiliary reservoir and back to the heated to the heated reservoir. Preferably, the liquid is fed to the process chamber under pressure and is removed from the process chamber by vacuum. Where the process chamber is maintained at atmospheric pressure the method and apparatus of the present invention minimize sample damage resulting from pressure changes.

BRIEF DESCRIPTION OF THE DRAWINGS

FIG. 5 is a detailed side view of the liquid container connected to the manifold.

DESCRIPTION OF THE PREFERRED EMBODIMENT

Figure 1:
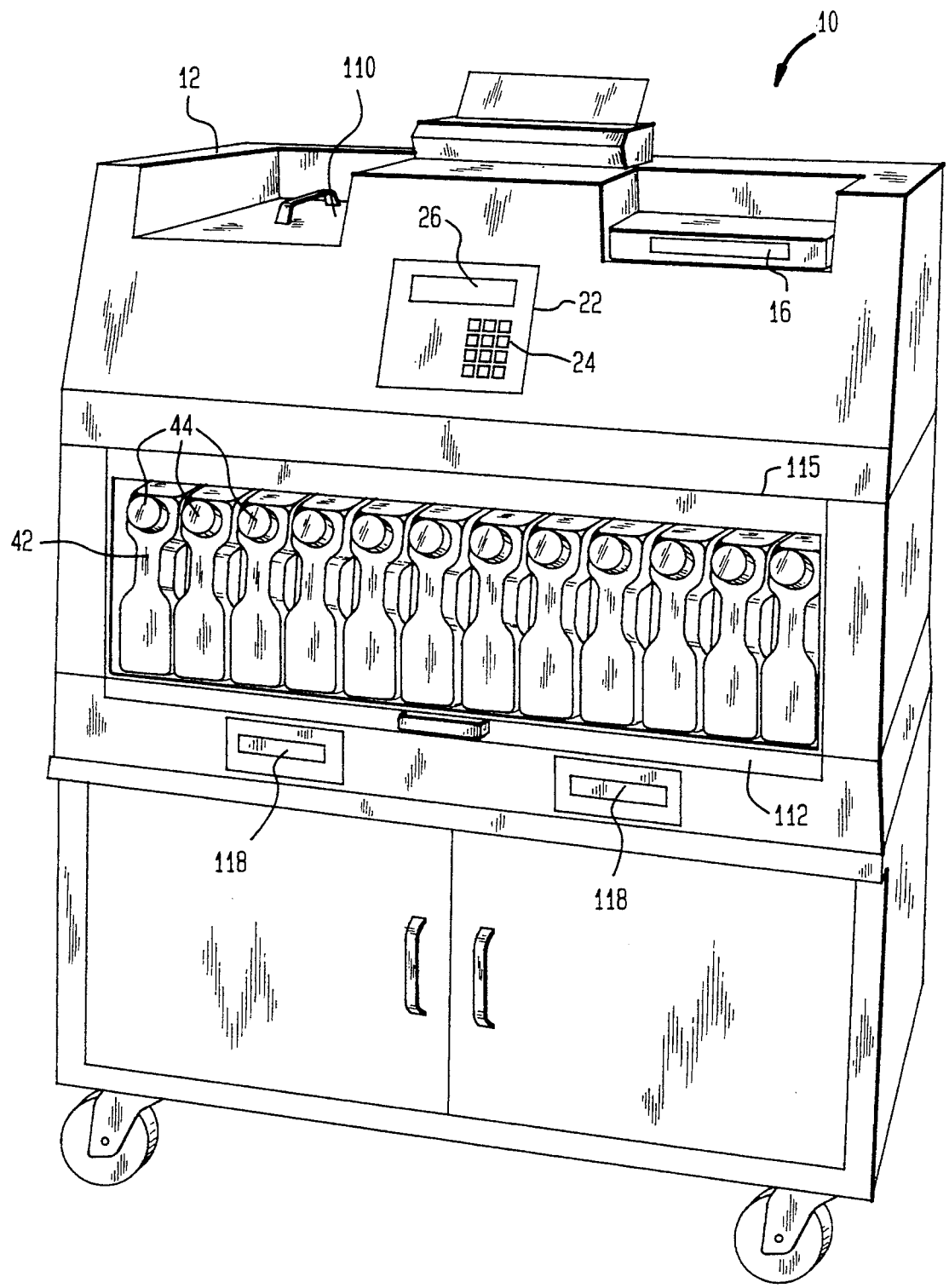
FIG. 1 is view in perspective of an assembled apparatus of the present invention.

A preferred embodiment of the present invention can be understood by those skilled in the art by reference to FIGS. 1 to 5. The tissue processor 10 of the present invention is constructed and operates to minimize tissue sample damage during processing of the tissue. FIG. 1 is a perspective view of the preferred tissue processor 10 in a housing or cabinet 12 which comprises a support frame 14.

The tissue is typically biological in nature and cut in sections for microscopic examination. The tissue processor is designed to process a plurality of tissue samples simultaneously in a sealed process chamber 16. The tissue samples can be located in the process chamber 16 on a plurality of tissue cassettes 18. The conditions in the process chamber 16, including the treatment materials, pressure and temperature are controlled by a suitable control means such as controller 20 comprising a computer microprocessor and a control panel 22 having a digital input keypad 24 and a display 26.

The process chamber 16 has at least one chamber inlet 28 preferably at or near the top of the process chamber 16, and at least one chamber outlet 30 preferably at or near the bottom of the process chamber 16. There is a pneumatic inlet 32 preferably at or near the top of the process chamber 16. The process chamber 16 can comprise a base 34 mounted on the frame 14. The base encloses .the chamber volume. There can be a process chamber cover 36 and a sealing means such as gasket 38 located to form a seal between cover 36 and base 34. There is a means to lock the cover 36 sealingly to the base 34. Heating means, preferably electrical heater are located at the sidewalls 40 of the base 34. The heating means are controlled by keypad 24 and controller 20.

The tissue samples mounted on cassettes 18 are place in the process chamber 16. A layer of tissue cassettes 18 is supported on a screen or perforated basket and placed in the chamber 16. Succeeding layers are place over each other with space for liquid in the processing chamber to contact each tissue sample.

The process chamber 16 containing the tissue specimens on the tissue cassettes 18 receives a predetermined sequence of liquids and molten paraffin, i.e., wax. The apparatus comprises at least one and preferably up to twenty liquid reservoirs 42 connected to communicate with the process chamber 16. Preferably, there are from eight to twenty liquid reservoirs.

A most preferred embodiment as shown in the Figures contains twelve reservoirs 42 which are plastic bottles as shown in FIGS. 1 and 5. The preferred reservoir bottles 42 comprise a bottle fill inlet 44 to an enclosed reservoir chamber 46 having bottle walls 48. The bottle 42 has has a process inlet 50. A reservoir hose 52 is sealingly connected to the process inlet 50. There is preferably a reservoir fitting 54 sealingly passing through the process inlet 50 to communicate with the process chamber 16. There can be an inlet housing 56 connected at the process inlet 50. The inlet housing 56 has an inlet housing passage 58 connected to the process inlet 50 and leads to a housing outlet 60. The housing outlet is sealing connected by a quick release fitting assembly 62 to manifold 64.

In the embodiment shown in FIG. 5 the quick release fitting assembly 62 comprises housing seal means such as O-ring 70 therebetween. Preferably, all of the reservoirs 42 are connected to the manifold 64. A manifold valve such as solenoid valve 72 can be connected between the housing outlet 60 and the manifold 64. The solenoid valve 64 is controlled by controller 20. In this way, different reservoirs 42 can be opened or closed to communication with the process chamber 16.

Most preferably, there is at least one auxiliary reservoir 74 between the liquid reservoirs 42 and the process chamber 16. The auxiliary reservoir 74 can be insulated or have heating means. Preferably, there is a second auxiliary reservoir 78 which can be also be insulated and/or heated. The second auxiliary reservoir 78 is also connected to communicate between the liquid reservoirs 42 and the process chamber 16. Auxiliary reservoirs 74, 78 are preferably enclosed.

The process chamber 16, manifold 64, and auxiliary reservoirs 74 and 78 are connected by hydraulic lines 80. Hydraulic solenoid valves 76 are placed in the hydraulic lines 80 to open and close flow through the lines 80.

Figure 2:
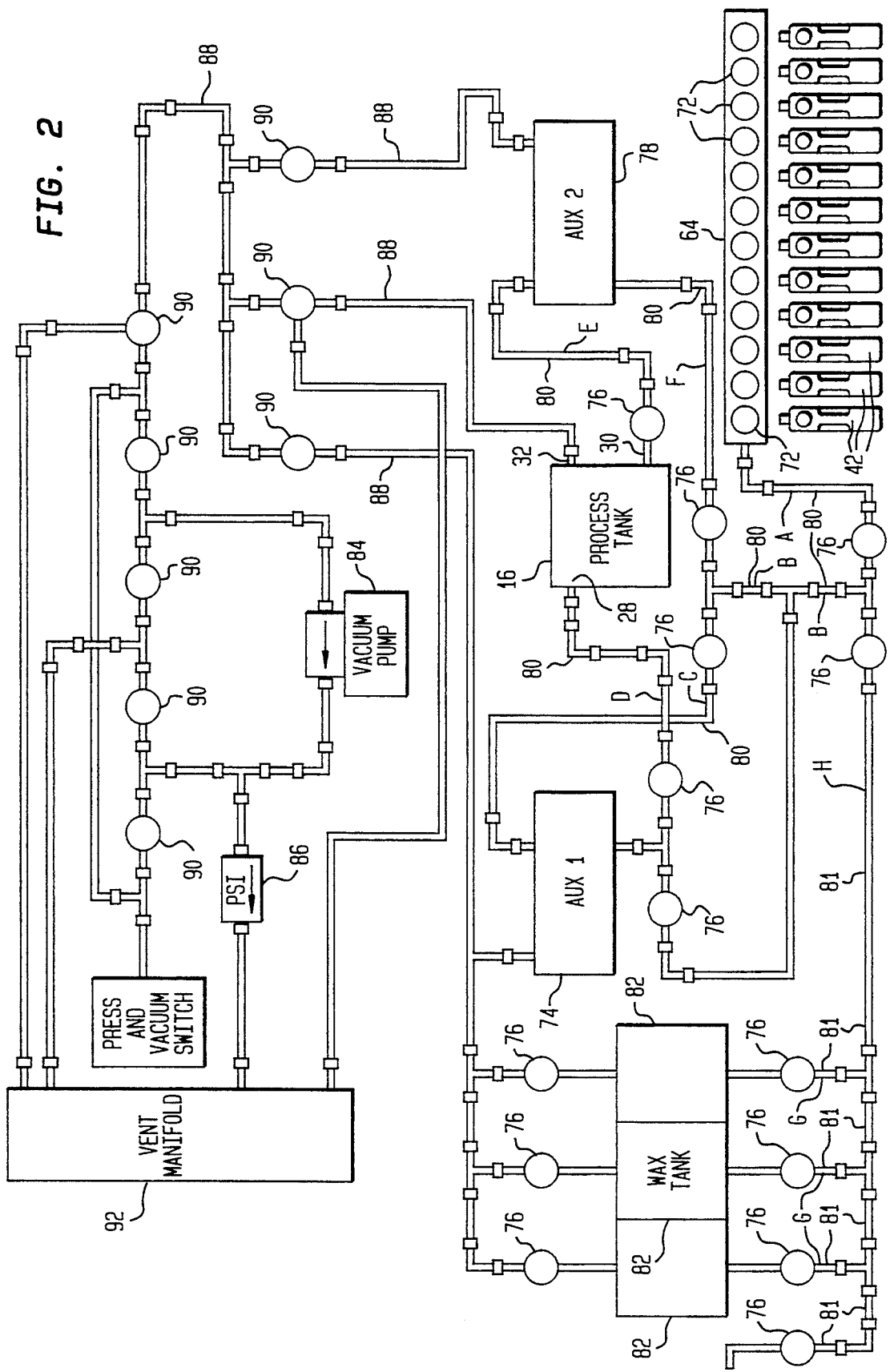
FIG. 2 is a schematic flow diagram of the present invention showing pneumatic and hydraulic flow.
Figure 3:
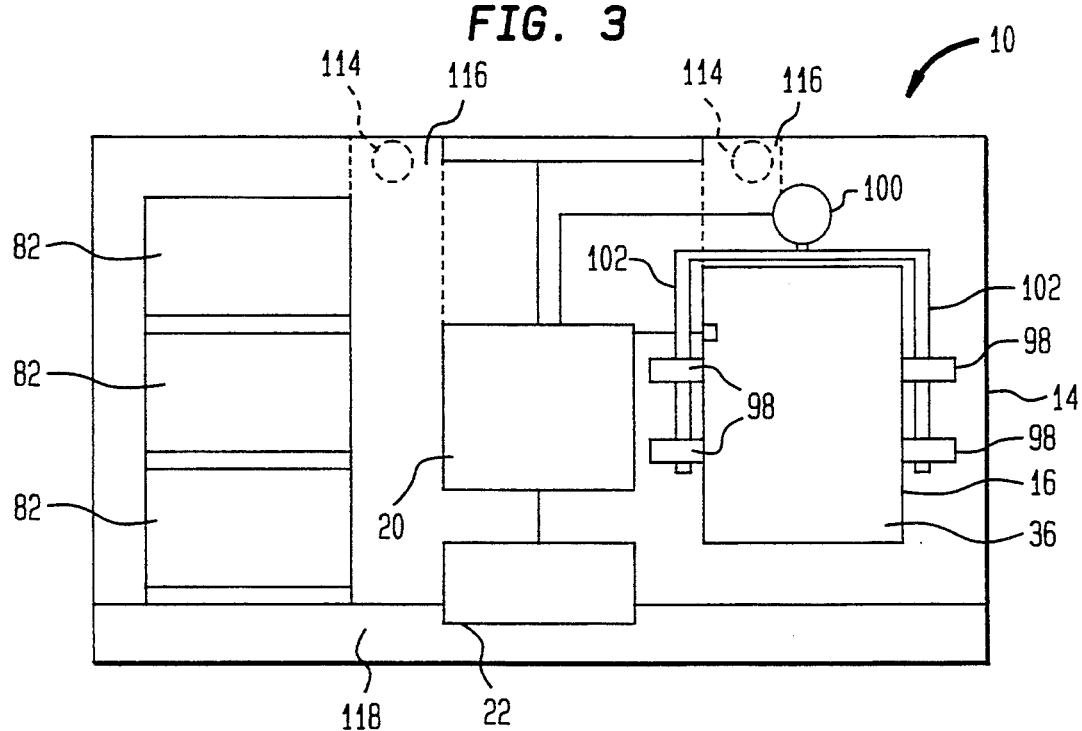
FIG. 3 is a top view of the apparatus with the upper section of the outer housing removed showing a lay out of the elements of a preferred embodiment.
Figure 4:
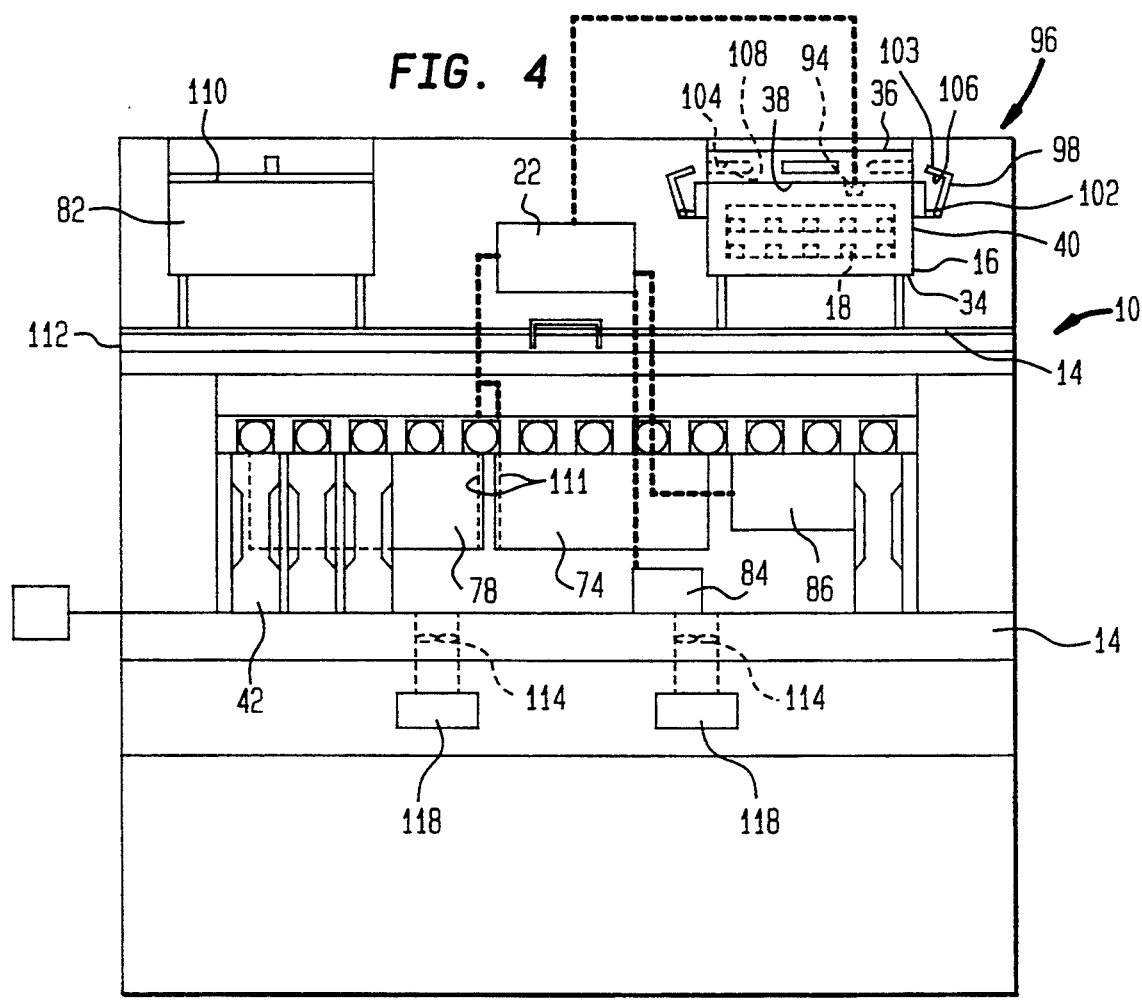
FIG. 4 is a front view of the apparatus with the upper section of the outer housing removed.

In addition to the liquid reservoirs 42 there is preferably at least one heated reservoirs 82. The heated reservoirs 82 are useful to heated and maintain molten paraffin. There are preferably two and more preferably three heated reservoirs 82. The heated reservoirs 82 are interconnected to communicate with the process chamber 16 through hydraulic lines 81 which can have soleniod valves 76 as shown in FIG. 2. Hydraulic lines 80 which provide common paths for liquid from reservoirs 42 and heated reservoirs 82 are also preferably heated.

There is a suitable means to drive liquid from the liquid reservoir 42 through the first auxiliary reservoir 42 to the process chamber 16. Similarly there can be a means to drive liquid from the process chamber 16 back to the liquid reservoir 42, preferably through the second auxiliary reservoir 78. There is also means to drive molten paraffin, considered to be liquid from the heated reservoir 82 through the first auxiliary reservoir 74 to the process chamber 16. Similarly, there can be a means to drive the molten paraffin back to the heated reservoir 82, preferably through the second auxiliary reservoir 78.

The means to drive the reagent liquids and the liquid paraffin to and from the process chamber 16 is preferably a pressure means such as a pneumatic pressure and vacuum pump 84. The pneumatic and vacuum pump 84 is interconnected to communicate with the process chamber, the auxiliary reservoirs 74, 78 and the heated reservoirs 82 through pneumatic lines 88 as shown in FIG. 2. There are pneumatic solenoid valves 90 located to open and close communication between the pressure and vacuum pumps and the process chamber and reservoirs. A vent manifold 92 is optionally interconnected to the pneumatic lines 88. Pressure relief valve 86 assures that the pressure in the pneumatic lines 88 does not exceed a preset value, preferably about 5 pounds per square inch.

The pneumatic and vacuum pump 84 can be used to drive the liquid from the liquid reservoir 42 through the first auxiliary reservoir 74 to the process chamber 16. The liquid is preferably driven from the reservoir 42 to the auxiliary reservoir 74 under vacuum. In this way, the reservoirs 42 can be made of plastic bottles, with the liquid "sucked out". The liquid is driven from the first auxiliary tank 74 to the process chamber 16 under pressure. This helps to rapidly fill the process chamber. The liquid is driven by the pneumatic and vacuum pump 84, preferably under vacuum from the process chamber 16 to the second auxiliary tank 78 under vacuum to remove the liquid without applying pressure to the process chamber 16 which, is maintained at atmospheric pressure. Preferably, pressure can be used to return the liquid to the liquid reservoirs 42 from the second auxiliary reservoir 78. The molten paraffin in the heated reservoirs 82 is transfer in the same manner with the lines through which it passes preferably heated to prevent freezing.

Because the liquids are fed and removed to process chamber 16 by vacuum and pressure means, there is means to sealingly close the process chamber lid 36. This means comprises a pressure sensor 94 to measure the pressure in the process chamber 16. The pressure sensor 94 communicates a signal related to the chamber pressure to controller 20. The controller 20 controls a means to lock 96 to lock or unlock the lid 36 on the process chamber 36. The preferred means to lock 96 comprises at least one latch 98 interconnected to and driven by motor 100. The latch is connected to latch shaft 102 which in turn is interconnected to the base 34 of the process chamber. When the controller 20 sends a signal to the motor 100 latch shafts 102 rotate causing latch extensions 103 to become inserted into or removed from latch slots 104. Latch slots 104 are shown in lid 36. However, the latches 98 can alternatively be connected to the lid 36 with the slots 104 located in the base 34. The latch extension 103 can contain means not only to lock the lid 36 to the base 34 but to force the lid to seal against the base. A preferred means is to have a tapered surface 106 which upon being inserted into the latch slot 104 forces the tapered surface 106 against the opposing slot insert surface 108.

The auxiliary reservoirs 74, 78 optionally and preferably has a liquid level sensor 111 which is interconnected to controller 20. This level sensor can be used to control the amount of fluid fed to the process chamber 12. For example, if two layer of cassettes 18 are placed in the chamber 16 the level of these layers is fed through the keypad. Only the level of liquid needed to immerse the two layer is introduced and removed. The chamber need not be completely filled and emptied between each sequential step of adding and removing treatment reagent or paraffin. Nor is it necessary to try to correlate the amount of liquid with a time to fill to a given level.

In order to prevent vapors from the system from leaking out into the environment, the apparatus is placed in a cabinet 12. The system is closed with a lid 110 on the heated reservoirs 82. The liquid reservoirs 42 are enclosed with easy access through door 112. Door 112 rotates up about a hinge means 115 and can be pushed back into the cabinet 12. There can be a filter system to circulate and filter the atmosphere in the cabinet before it reenters the environment. This can be accomplished by the use of fans 114 which direct the atmosphere in the cabinet 12 into channels 116. The atmosphere is forced through filters 118, preferably charcoal filters, and into the environment. The filters 118 are located in the front of the cabinet for easy access and can be pulled out for replacement or cleaning.

The apparatus of the present invention permits flexibility of operation. A preferred method of operation comprises maintaining reagent liquid in liquid reservoirs 42. At least one tissue specimen is placed in the process chamber 16. The process chamber 16 is sealingly closed.

The process chamber 16 is maintained at a desired temperature. A sequential program is selected to control the feeding and removal of at least one liquid reagent from liquid reservoirs 42 and paraffin from heated reservoirs 82 as desired. Pressure or vacuum is used to drive the liquids to a first auxiliary reservoir 74, with pressure from pump 84 preferred. The liquid from the first auxiliary reservoir 74 is then driven to the process chamber 16. Upon completion of a predetermined immersion time the liquid in the process chamber 16 is driven to the second auxiliary chamber 78. This is accomplished by either a pressure or a vacuum drive, with removal preferably accomplished by vacuum. The vacuum is provided by vacuum pump 84.

The flow of liquid reagent from liquid reservoirs 42 and paraffin heated reservoirs 82 is illustrated by reference to FIG. 2. During an example operation, liquid reservoirs 42 sequentially open to communication through lines A, B and C to auxiliary reservoir 74. Liquid reagent is driven by vacuum to auxiliary reservoir 74. Line D opens and liquid is driven under pressure of about 5 psi to process chamber 42. At the completion of the period of exposure of the sample to the liquid in process chamber 42, line E opens and there is communication between process chamber 16 through line E to auxiliary reservoir 78. The liquid is driven from process chamber 16 to auxiliary reservoir under a vacuum. Lines F, B and A open communication between auxiliary reservoir 78 to liquid reservoirs 42 to which the liquid is driven under pressure of about 5 psi. Molten paraffin flows analogously. Heated reservoirs 82 to auxiliary reservoir 74 through lines G, H and B. Molten paraffin flows from heated reservoirs 82 to auxiliary reservoir 74 through the open lines under a vacuum. Line D opens and there is communication between auxiliary reservoir 74 and process chamber 16 through which the molten paraffin is driven under pressure of about 5 psi. The process chamber 16 is emptied to auxiliary reservoir 78 under vacuum through line E which opens. Lines F, B, H and G open communication between auxiliary reservoir 78 to heated reservoirs 82 to which the molten paraffin is driven under pressure.

During the operation the use of the auxiliary reservoirs maintains the liquid for each subsequent step ready to be fed. This includes heated paraffin. This helps to minimize time between steps. Additionally, when a liquid such as paraffin requires heating this can be accomplished remote from the process chamber 16. In this way the heated reservoirs are not adjacent to the process chamber 16. The process chamber 16 can have its temperature controlled solely by the temperature of the liquid and the process chamber heating means 40.

The apparatus and method of the present invention can be used to treat biological samples and prepare them for microscopic evaluation. Useful fluids include Zenker's solution, water, xylene, formalin, alcohol and the like. A typical operation involves cycles using the following liquid sequence: formalin, 70% alcohol, 80% alcohol, 95% alcohol, absolute alcohol, absolute alcohol, xylene, xylene, paraffin I, paraffin II, paraffin III, followed by a cleaning sequence of xylene, absolute alcohol and water. The apparatus can operate at typical processing temperatures and pressures to treat a specific sample with little or no damage.

While the preferred embodiments of the invention is described above the claimed scope of the invention follows.

What is claimed is:

1. A tissue processor apparatus comprising:
   a support frame;
   a tissue processor process chamber supported on the frame;
   at least one liquid reservoir;
   at least one first auxiliary reservoir connected between the process chamber and the at least one liquid reservoir;
   at least one second auxiliary reservoir connected between the process chamber and the at least one liquid reservoir;
   means to drive liquid from the at least one liquid reservoir to the first auxiliary reservoir, from the first auxiliary reservoir to the process chamber, from the process chamber to the second auxiliary reservoir, and from the second auxiliary reservoir to the at least one liquid reservoir.

2. The apparatus as recited in claim 1 wherein the means to drive liquid is selected from the group consisting of a pressure means, a vacuum means or a combination of pressure and vacuum means.

3. The apparatus as recited in claim 2 wherein the pressure means is a pneumatic pump and the vacuum means is a vacuum pump.

4. The apparatus as recited in claim 2 wherein the means to drive liquid from at least one liquid reservoir to the first auxiliary reservoir is the vacuum means, the means to drive liquid from the first auxiliary reservoir to the process chamber is a pressure means, the means to drive liquid from the process chamber to the second auxiliary reservoir is the vacuum means, and the means to drive liquid from the second auxiliary reservoir to at least one liquid reservoir is a pressure means.

5. The apparatus as recited in claim 1 further comprising at least one heated reservoir connected to the process chamber through the first and second auxiliary reservoirs.

6. The apparatus as recited in claim 1 wherein the process chamber has a vent to the atmosphere, whereby the pressure in the process chamber can be maintained at atmospheric pressure.

7. The apparatus as recited in claim 5 wherein the heated reservoirs are located to minimize heat transfer with the process chamber.

8. The apparatus as recited in claim 1 wherein there are a plurality of liquid reservoirs and a plurality of heated reservoirs.

9. The apparatus as recited in claim 8 wherein there are from 8 to 20 liquid reservoirs and 2 to 5 heated reservoirs.

10. The apparatus as recited in claim 8 further comprising a liquid manifold connected to communicate with the plurality of liquid reservoirs.

11. The apparatus as recited in claim 10 wherein the liquid reservoirs are connected to the manifold by a quick connect and disconnect means.

12. The apparatus as recited in claim 1 further comprising a means to measure and control the fluid level of in the process chamber.

13. The apparatus as recited in claim 1 wherein the tissue processor process chamber is temperature controlled.

14. An apparatus comprising:
    a support frame;
    a temperature controlled process chamber supported on the frame;
    a manifold connected to communicate with the process chamber;

at least two liquid reservoirs, with each liquid reservoir connected to communicate with the process chamber through the manifold;

at least two auxiliary reservoirs, at least one first auxiliary reservoir and at least one second auxiliary reservoir, with each reservoir separately connected between the process chamber and the manifold; and means to drive liquid from at least one of the at least two liquid reservoirs to the first auxiliary reservoir, from the first auxiliary reservoir to the process chamber, from the process chamber to the second auxiliary reservoir, and from the second auxiliary reservoir to at least one of the at least two liquid reservoirs.

15. The apparatus as recited in claim 14 further comprising a quick connect and disconnect means to connect the liquid reservoirs to the manifold.

16. A tissue processor apparatus comprising:
a support frame;
a temperature controlled tissue processor process chamber supported on the frame;
a process chamber cover;
a sealing means between the chamber cover and the chamber;
at least one liquid reservoir, with each liquid reservoir connected to communicate with the process chamber;
at least two auxiliary reservoirs, at least one first auxiliary reservoir and at least one second auxiliary reservoir, with each reservoir separately connected between the process chamber and at least one reservoir;
means to drive liquid from the at least one liquid reservoir to the first auxiliary reservoir, from the first auxiliary reservoir to the process chamber, and means to drive liquid from the process chamber to the second auxiliary reservoir, and from the second auxiliary reservoir to the at least one liquid reservoir;
a pressure sensor in the process chamber to measure the pressure and generate a pressure signal; and
a means to lock and unlock the cover of the process chamber in response to the pressure signal.

17. The apparatus as recited in claim 16 wherein the means to lock comprises at least one motor driven latch which secures the cover to the chamber.

* * * * *